(12) United States Patent
Nadon et al.

(10) Patent No.: US 10,736,546 B2
(45) Date of Patent: Aug. 11, 2020

(54) METHOD AND DEVICE FOR CONTINUOUS IN-EAR HEARING HEALTH MONITORING ON A HUMAN BEING

(71) Applicant: EERS GLOBAL TECHNOLOGIES INC., Montréal (CA)

(72) Inventors: Vincent Nadon, Deux-Montagnes (CA); Jérémie Voix, Montréal (CA); Annelies Bockstael, Ghent (BE); Dick Botteldooren, De Pinte (BE); Jean-Marc Lina, Montréal (CA)

(73) Assignee: EERS GLOBAL TECHNOLOGIES INC., Montréal, Québec (CA)

( * ) Notice: Subject to any disclaimer, the term of this patent is extended or adjusted under 35 U.S.C. 154(b) by 0 days.

(21) Appl. No.: 16/723,956

(22) Filed: Dec. 20, 2019

(65) Prior Publication Data

US 2020/0138340 A1 May 7, 2020

Related U.S. Application Data

(62) Division of application No. 15/319,934, filed as application No. PCT/CA2015/000401 on Jun. 19, 2015, now Pat. No. 10,548,516.

(Continued)

(51) Int. Cl.
*H04R 25/00* (2006.01)
*A61B 5/12* (2006.01)
(Continued)

(52) U.S. Cl.
CPC .......... *A61B 5/125* (2013.01); *A61B 5/7203* (2013.01); *A61B 5/725* (2013.01); *A61F 11/08* (2013.01);
(Continued)

(58) Field of Classification Search
CPC ....... A61B 5/125; A61B 5/7203; A61B 5/725; A61B 5/0476; A61B 5/048;
(Continued)

(56) References Cited

U.S. PATENT DOCUMENTS 5,776,179 A 7/1998 Ren et al.
5,792,073 A * 8/1998 Keefe .................... A61B 5/121
600/559

(Continued)

OTHER PUBLICATIONS

Wing-Kin Ma et al, "Estimation of Distortion Product Otoacoustic Emissions", IEEE Transactions on Biomedical Engineering, IEEE Service Center, Piscataway NJ, USA, vol. 46, No. 10, Oct. 1, 1999, XP011006777, ISSN: 0018-9294.

(Continued)

*Primary Examiner* — Xu Mei
(74) *Attorney, Agent, or Firm* — PRAXIS

(57) ABSTRACT

A device and method for the continuous monitoring of otoacoustic emissions (OAE) levels on an individual worker uses as a pair of earpieces each featuring an external microphone, an internal microphone and a pair of miniature receivers. An adaptive filtering noise rejection processing of the measured distortion product OAE (DPOAE) is used to further improve the Signal-to-Noise ratio in frequencies where passive isolation remains insufficient. The adaptive filtering noise rejection technique relies on a Normalized Least-Mean-Square (NLMS) algorithm that uses the ipsilateral external microphone and the contralateral internal microphone to reject the noise from the measured DPOAE signals for each in-ear OAE probe. A DPOAE signal extraction algorithm provides for an increase in results reliability on a greater dynamic range in DPOAE magnitudes than known methods of DPOAE signal extraction. The device and method is suitable for the continuous monitoring of (Continued)

workers' hearing capabilities in industrial noises up to 75 dB(A).

20 Claims, 3 Drawing Sheets

Related U.S. Application Data

(60) Provisional application No. 62/014,327, filed on Jun. 19, 2014.

(51) Int. Cl.
*A61F 11/08* (2006.01)
*A61B 5/00* (2006.01)
*A61F 11/06* (2006.01)

(52) U.S. Cl.
CPC ............ *A61F 11/06* (2013.01); *H04R 25/353* (2013.01); *H04R 25/356* (2013.01); *H04R 2225/025* (2013.01)

(58) Field of Classification Search
CPC ....... A61B 5/04845; A61B 5/12; A61B 5/121; A61B 5/123; A61B 5/126; A61B 5/128; A61F 11/06; A61F 11/08; H04R 25/356; H04R 25/453; H04R 25/502; H04R 25/505; H04R 25/652; H04R 25/30; H04R 25/305; H04R 25/70; H04R 2225/025; H04R 2225/43
USPC ....... 381/312, 316, 317, 318, 320, 321, 328, 381/60; 600/559; 607/55, 57
See application file for complete search history.

(56) References Cited

U.S. PATENT DOCUMENTS

| | | | |
|---|---|---|---|
| 6,123,677 A * | 9/2000 | Heitmann | A61B 5/12 600/559 |
| 7,223,245 B2 | 5/2007 | Zoth et al. | |
| 8,254,586 B2 | 8/2012 | Voix et al. | |
| 10,548,516 B2 * | 2/2020 | Nadon | A61F 11/08 |
| 10,561,347 B2 * | 2/2020 | Dalhoff | A61B 5/125 |
| 2002/0143242 A1 | 10/2002 | Nemirovski | |
| 2004/0133371 A1 | 7/2004 | Ziarani | |
| 2012/0177209 A1 * | 7/2012 | Goldstein | A61B 5/121 381/56 |
| 2014/0114209 A1 | 4/2014 | Lodwig | |
| 2017/0332977 A1 * | 11/2017 | Dalhoff | A61B 5/7203 |
| 2019/0159702 A1 * | 5/2019 | Charaziak | A61B 5/6817 |

OTHER PUBLICATIONS

Ma W K et al, "Adaptive Filtering for Distortion Product Otoacoustic Emissions", Engineering in Medicine and Biolog Society, 1996, Bridging discipline s for Biomedicine, 18th Annual International Conference of the IEEE Amsterdam, Netherlands, Oct. 31, 1996, pp. 1524-1525, XP010261912, DOI: 10.1109/IEMBS.1996. 647534, ISBN: 978-0-7803-3811-1.

Whitehead, et al. "Measurement of Otoacoustic Emissions for Hearing Assessment", May 1994, IEEE Engineering in Medecine and Biology, p. 210-225.

* cited by examiner

METHOD AND DEVICE FOR CONTINUOUS IN-EAR HEARING HEALTH MONITORING ON A HUMAN BEING

CROSS-REFERENCE TO RELATED APPLICATIONS

This application is a divisional application of U.S. patent application Ser. No. 15/319,934 filed on Dec. 19, 2016 and which is a U.S. national stage entry of PCT Application Serial No. PCT/CA2015/000401 filed on Jun. 19, 2015 claiming benefit of U.S. Provisional Application for Patent Ser. No. 62/014,327 filed on Jun. 19, 2014, all three being incorporated herein by reference.

FIELD OF THE INVENTION

The present invention relates to hearing protection, and more specifically to a method and device for continuous in-ear hearing health monitoring on a human being based on measurements of otoacoustic emissions (OAE).

BACKGROUND OF THE INVENTION

Occupational hearing loss remains a problem, despite the efforts made by implementing hearing conservation programs in the workplace. The first issue is that the actual passive noise reduction of the hearing protector worn during the work shift greatly differs from the optimal passive noise reduction measured in the laboratory due to suboptimal placement, inconsistent use and in general variations in the acoustical seal over time. Despite the recent development of a field attenuation measurement system for hearing protection devices, the precise residual noise level under the hearing protector remains unknown. The second issue is that, even if this individual noise exposure would be known precisely for each worker, the effective risk of hearing damage would still remain uncertain given the difference between worker's susceptibility to develop noise-induced hearing loss.

To address simultaneously these two issues, an alternative approach would consist in measuring the auditory health changes induced by daily noise exposure on an individual basis and to immediately warn the worker (in real-time) when a change in hearing sensitivity is taking place, before any permanent damage is caused. In clinical practice, a wide range of audiological tests are available to assess hearing status. However, with respect to occupational noise exposure, these tests are not conducted frequently enough for early detection of changes in hearing sensitivity induced by noise exposure, and also not sufficiently robust to be carried out in an environment where acoustical and electrical noise intensity levels are too high. Moreover, the whole procedure to monitor a worker's hearing health daily takes too much time for most standard audiological tests and would interfere with the worker's work routine.

Indeed, distortion product otoacoustic emissions (DPOAEs) offer an objective, fast and reliable way to detect early signs of noise-induced changes in hearing sensitivity. When two pure tone stimuli, $f_1$ and $f_2$ with the $f_2/f_1$ ratio typically around 1.22, are sent through the two miniature receivers of the otoacoustic emission (OAE) probe, low-level cubic distortion signals (i.e. $f_{dp}=2f_1-f_2$) are generated by an active non-linear process inside the inner ear. These signals travel back from the inner ear to the outer ear canal where they can be recorded. If the outer hair cells inside the cochlea of the inner ear are damaged—for instance due to previous excessive noise exposure—the amplitude of DPOAEs is found to be lower than if they would be healthy.

Nevertheless, various clinical test setups for DPOAEs have been commercially available for more than 15 years, now ranging from standalone all-in-one hand-held devices to more advanced systems with two probe measurement interfaces connected to a personal computer. No commercial system currently on the market can continuously monitor DPOAEs in a given individual, in field conditions, because the nominal DPOAE signal, generally at levels between −5 dB to 20 dB sound pressure levels (SPL) is disturbed by the background noise. Proper recording of DPOAE responses is very vulnerable to interfering background noise which normally largely exceeds these low level responses.

In the case of hardware solutions, standard probe eartips usually provide a certain amount of passive noise reduction, but this noise reduction is not individually optimized and it is not sufficient for noisy test environments. Even though passive earmuffs could be used on top of the DPOAE probe, they may not provide sufficient additional low frequency attenuation in order to measure DPOAEs accurately in industrial environments. Unfortunately, placing an earmuff on top of an OAE probe might slightly dislocate the probe and hence require more strict supervision of calibration procedures. This situation would conflict with the final aim of OAE monitoring without any external supervision.

In the case of software solutions, the standard noise rejection techniques and time averaging can improve the signal-to-noise ratio (SNR) in case of limited disturbance, but this has shown to be insufficient in more realistic occupational noise settings. Moreover, these techniques do not offer sufficient improvement to lower the noise floor in the frequency range below 1500 Hz to measure DPOAEs accurately even in lower background noise levels.

In response to the problems encountered with averaging methods, several adaptive filtering techniques have been studied. Delgado's adaptive filtering technique uses a contralateral internal ear microphone (IEM) as a physiological noise reference and an ipsilateral outer ear microphone (OEM) as an external background noise reference to remove the noise captured in the tested ear IEM. This adaptive filtering algorithm was proven to increase the SNR on the whole frequency spectrum while reducing the test time needed by normal time averaging methods. Although Delgado's adaptive filtering does lower the noise level in the DPOAE signal, it has not been tested in realistic noise conditions and a somewhat low signal-to-noise ratio improvement was obtained with laboratory setup experiments.

Furthermore, although additional passive noise reduction and other hardware improvements might improve the Signal-to-Noise ratio (SNR), studies have shown that in order to extract the level of the DPOAE signal in a noisy environment, a more robust signal processing scheme is needed.

In order to extract the level of the DPOAE signal after the noise rejection processing, a robust sinusoid (or tonal) signal extraction algorithm is needed. Previous studies have shown a promising approach to extract DPOAE signals without the need of a Fast Fourier Transform (FFT). This approach is more robust to higher noise levels and, since it is not FFT based, it can be used at any stimuli frequency (respecting the 1.22 ratio) without having to keep an integer multiple of the frequency resolution (Δf) of the FFT to reduce the spectral leakage. The extended stimuli frequency range capabilities of such an algorithm, may give the opportunity for researchers to characterize the cochlea with a finer frequency resolution than FFT based algorithms.

Also, it has been shown that a previously proposed algorithm is very sensitive to the adjustment of various parameters i.e. filter adjustments, adaptation step sizes and normalization gains in order to optimize the algorithm for all possible situations such as, for example, different DPOAE magnitudes and various noise conditions. Therefore, such an algorithm is not practical to assess a worker's cochlea functionality in an automatic and autonomous manner if parameters need to be changed constantly.

While the noise rejection algorithm and the involved hardware does lower the noise floor and increase the DPOAE level reliability, the alternative to the FFT based DPOAE level extraction can also contribute to reduce the noise level since the FFT is very sensitive to background noise in frequency bins near the DPOAE frequency and the stimuli. The magnitude of the stimuli, noise signals and DPOAE response causes spectral leakage around the DPOAE frequency which introduces an error in the estimation of the DPOAE level when the DPOAE frequency is not an integer multiple of the frequency resolution ($\Delta f$). A method to solve these problems has been proposed to extract non-stationary sinusoids with a non FFT based algorithm, but is too sensitive to the adjustment of various parameters and therefore unrealistic to use.

According to the results obtained in previous studies, there is a need for an improved method and device for continuous in-ear hearing health monitoring on a human being based on measurements of otoacoustic emissions (OAE) in order to use such device for in-field applications.

SUMMARY OF THE INVENTION

It is therefore a general object of the present invention to provide an improved method and device for continuous in-ear hearing health monitoring on a human being based on measurements of otoacoustic emissions (OAE), that substantially solve the above-mentioned problems and drawbacks.

An advantage of the present invention is that the method and device allow a precise real-time variation assessment in hearing status of a given worker through the development of an in-ear hearing protection device—in-ear meaning positioned in the ear canal—featuring in-field otoacoustic emission (OAE) monitoring, more specifically the measurement of Distortion Product OAE (DPOAEs).

Another advantage of the present invention is that the method and device use an adaptive filtering algorithm consisting in a cascaded two stage adaptive algorithm with a specific positioning of the microphones to enhance the noise rejection performance. This approach aims to improve DPOAE detection by using three microphones simultaneously: the tested ear internal microphone, the contralateral internal microphone and the reference microphone mounted flush on the outer faceplate of the earpiece-embedded OAE probe. For the adaptive filtering algorithm, two new techniques are used in the present invention: first the influence of the external microphone position is accounted for in order to improve noise rejection performance; secondly, an adaptive filter identification step is used to characterize the probe attenuation transfer function and inter-probe transfer function in the adaptive filtering algorithm and the use of a normalized version of the Least-mean square (LMS) algorithm to again improve noise rejection in the signal.

Yet another advantage of the present invention is that the method and device extract nonstationary sinusoids with a temporal modulation algorithm that extracts DPOAE signal magnitude, rather than with a FFT based algorithm. The combination of the adaptive filtering algorithm with the DPOAE signal extraction technique of the present application is new compared to actual DPOAE processing methods.

Yet another advantage of the present invention is that the method and device use a DPOAE measurement system capable of (a) achieving accurate DPOAE response estimation in (b) elevated background noise by combining improved signal detection algorithms using an advanced noise rejection approach, at least with background noise fragments between about 65 and about 75 dB(A).

A further advantage of the present invention is that the method and device use an algorithm for the extraction of DPOAE levels that is implemented in a low cost digital signal processor (DSP) with simplified structure, and using a temporal modulation with amplitude and phase tracking capabilities in order to accurately extract the DPOAE signal level. Within the same algorithm, a noise estimator can be used in order to evaluate the SNR of the DPOAE signal in the DSP. The processing scheme, without FFT, can use an extended range of stimuli frequencies to precisely characterize the health of the cochlea's finer structure.

Yet another advantage of the present invention is that the method and device use an adaptive filtering noise rejection algorithm that reduce the ambient and physiological noises from the DPOAE signal using three microphones simultaneously: the first microphone capturing the DPOAE signal inside the outer ear canal, the second microphone placed inside the contralateral ear canal, and the third microphone placed at the vicinity (within a distance of about 15 cm, and more preferably within 10 cm) of the tested ear DPOAE probe to capture the external noise.

Still another advantage of the present invention is that the method and device use a pair of earpieces, typically in-ear devices at least partially located into the outer ear canals, and preferably custom-fitted in-ear devices occluding the outer ear canals as described in U.S. Pat. No. 7,864,972 to McIntosh et al. issued on Jan. 4, 2011, combining simultaneously hearing protection and otoacoustic emissions. Custom-fitted in-ear devices are preferably considered since they provide maximum passive attenuation of ambient noise and reduced placement and fit variability, therefore well suited for enabling continuous monitoring of one's hearing health status, in 'real-world' noisy industrial environment, and prevent noise-induced hearing loss.

Yet another advantage of the present invention is that the device and method include an output media onto which the different output results are provided and/or displayed which be any known media, and preferably portable media, such as, but not limited to, laptop computers, tablets, smartphones, personal digital assistants (PDAs), or the like.

According to an aspect of the present invention there is provided a signal amplitude extraction method for providing a magnitude of a pre-filtered signal ($s(n)$) of a distortion product otoacoustic emission (DPOAE) for a continuous in-ear hearing health monitoring on a human being, the method comprising the steps of:

acquiring the DPOAE signal ($s(n)$) having a DPOAE frequency ($f_{dp}$);

generating a carrier signal ($c_1(n)$) having a carrier frequency ($f_c$) about equal to the DPOAE frequency ($f_{dp}$);

normalizing the carrier signal ($c_1(n)$) with amplitude and phase tracking of the DPOAE signal ($s(n)$) to obtain a normalized modulating carrier signal ($c_1'(n)$);

temporally modulating the DPOAE signal ($s(n)$) with the normalized modulating carrier signal ($c_1'(n)$) to set a constant magnitude modulated DPOAE signal ($m_1(n)$); and providing the constant magnitude modulated DPOAE signal ($m_1(n)$) as a DPOAE magnitude output signal.

In one embodiment, the method, for providing a magnitude of a noise signal around a frequency of the DPOAE signal ($s(n)$), further includes the steps of:
- transposing the carrier signal ($c_2(n)$) in frequency, by a frequency step, to obtain a frequency transposed carrier signal ($c_2'(n)$);
- temporally modulating the DPOAE signal ($s(n)$) with the frequency transposed carrier signal ($c_2'(n)$) to get the magnitude of the noise signal ($m_2(n)$) around the DPOAE signal ($s(n)$); and
- providing the magnitude of the noise signal ($m_2(n)$) as a noise output signal.

In one embodiment, the method further includes the step of averaging the constant magnitude modulated DPOAE signal ($m_1(n)$) with a running Root-Mean-Square (RMS) algorithm.

Conveniently, wherein the step of averaging converges within about 0.2 second.

In one embodiment, the constant magnitude modulated DPOAE signal ($m_1(n)$) is a 0-5 Hz signal ($m_1(n)$), and preferably a 0 Hz signal ($m_1(n)$).

In one embodiment, the pre-filtered DPOAE signal ($s(n)$) is being pre-filtered with a noise rejection adaptive filter.

Conveniently, the noise rejection adaptive filter includes inner-ear and outer-ear adaptive filters.

In one embodiment, the frequency step varies from about 5 Hz to about 100 Hz, and is preferably about 50 Hz.

According to another aspect of the present invention there is provided a device for continuous in-ear hearing health monitoring on a human being, the device comprising:
- a pair of earpieces, each said earpiece including an internal microphone (IEM-I, IEM-C) adapted to be in fluid communication with an outer ear canal of an ear of a user, an outer ear microphone (OEM-I, OEM-C) adapted to be in fluid communication with an adjacent environment outside the ear of the user, and first and second receivers adapted to be in fluid communication with the outer ear canal;
- a controller system connecting to both the first and second receivers of at least one said pair of earpieces for simultaneously sending first ($f_1(n)$) and second ($f_2(n)$) stimuli sound signals thereto, respectively, the controller system connecting to the internal and outer ear (IEM-I, OEM-I) of one said earpieces corresponding the a tested ear of the user and to the internal (IEM-C) microphone of the other one said earpieces for recording respective inner ($d_1(n)$), outer ($x_2(n)$) and inner ($x_1(n)$) sound signals therefrom; and
- an output media connected to the controller system for providing a resulting magnitude of a distortion product otoacoustic emission (DPOAE) signal calculated by the controller system using a noise rejection algorithm and a signal extraction algorithm based on a carrier signal ($c(n)$) at a frequency of the DPOAE signal established using the first ($f_1(n)$) and second ($f_2(n)$) stimuli sound signals.

In one embodiment, the outer ear microphone (OEM-I, OEM-C) are adapted to be located within a 15 cm distance from the outer ear of the user, and preferably within a 10 cm distance from the outer ear of the user.

In one embodiment, the controller system includes a band-pass filter set at the frequency of the DPOAE signal to enhance the DPOAE signal as an input to the signal extraction algorithm.

In one embodiment, the controller system includes a low-pass filter set at a predetermined frequency to condition at least one of the outer ($x_2(n)$) sound signal of the outer ear microphone (OEM-I) and the inner ($x_1(n)$) sound signal of the internal microphone (IEM-C) before calculation of the DPOAE signal with the controller system using the noise rejection algorithm.

In one embodiment, the output media is a portable output media.

In one embodiment, the controller system is a portable controller system and the output media is a display of the portable controller system.

According to another aspect of the present invention there is provided a method for continuous in-ear hearing health monitoring on a human being based on measurements of distortion product otoacoustic emission (DPOAE) signals and using a pair of first and second earpieces, each said earpiece having an internal microphone (IEM-I, IEM-C) adapted to be in fluid communication with an outer ear canal of an ear of a user, an outer ear microphone (OEM-I, OEM-C) adapted to be in fluid communication with an adjacent environment outside the ear of the user, and first and second receivers adapted to be in fluid communication with the outer ear canal, the method comprising the steps of:
- a) sending simultaneously first ($f_1(n)$) and second ($f_2(n)$) stimuli sound signals to the first and second receivers of the first earpiece of a tested ear of the user, respectively;
- b) simultaneously recording respective inner ($d_1(n)$) and outer ($x_2(n)$) sound signals from the internal and outer ear microphones (IEM-I, OEM-I) of the first earpiece and an inner sound signal ($x_1(n)$) from the internal microphone (IEM-C) of the second earpiece; and
- c) processing the inner ($d_1(n)$, $x_1(n)$) and outer ($x_2(n)$) sound signals of said first and second earpieces to obtain a resulting distortion product otoacoustic emission (DPOAE) signal based on the first ($f_1(n)$) and second ($f_2(n)$) stimuli sound signals and using a noise rejection algorithm followed by a signal extraction algorithm.

In one embodiment, the method further includes, before step a), the steps of:
- initializing an inter-probe transfer function of a first adaptive filter using the internal (IEM-I, IEM-C) microphones of the first and second earpieces and a probe attenuation transfer function of a second adaptive filter using the internal (IEM-I) and outer ear (OEM-I) microphones of the first earpiece when only an external wide-band sound signal is being sent to an external loudspeaker for a pre-determined time duration;
- sending only an external wide-band sound signal to an external loudspeaker;
- activating an adaptation of the inter-probe transfer function using the respective inner sound signals ($d_1(n)$, $x_2(n)$) measured from the internal (IEM-I, IEM-C) microphones of the first and second earpieces and the probe attenuation transfer function using the respective inner ($d_1(n)$) and outer ($x_2(n)$) sound signals measured from the internal (IEM-I) and outer ear (OEM-I) microphones of the first earpiece with the external wide-band sound signal for a pre-determined time duration; and
- stopping sending the external wide-band sound signal and the adaptation of the inter-probe and probe attenuation transfer functions;
- wherein the initialized inter-probe transfer function of the first adaptive filter and the initialized probe attenuation transfer function of the second adaptive filter are used by the noise rejection algorithm in the processing step c).

In one embodiment, the step of activating an adaptation includes using a convergence step size varying between about 0.0001 and about 0.7.

In one embodiment, the external wide-band sound signal covers a frequency range extending between about 20 Hz and about 20 kHz.

In one embodiment, step c) further includes processing a noise rejection filtered DPOAE signal with a band-pass filter set at the frequency of the DPOAE signal to enhance the DPOAE signal as an input to the signal extraction algorithm.

In one embodiment, step c) further includes processing at least one of the outer ($x_2(n)$) sound signal of the outer ear microphone (OEM-I) and the inner ($x_1(n)$) sound signal of the internal microphone (IEM-C) with a low-pass filter set at a predetermined frequency to condition before processing the inner ($d_1(n)$, $x_1(n)$) and outer ($x_2(n)$) sound signals of said first and second earpieces using the noise rejection algorithm.

In one embodiment, the method further includes the step of:

d) providing the resulting DPOAE signal onto an output media.

In one embodiment, the step of providing includes providing the resulting DPOAE signal onto a portable output media.

In one embodiment, the pre-determined time duration varies between about 1 s and about 300 s, and preferably about 120 s.

According to another aspect of the present invention there is provided a signal noise rejection method for providing a signal ($s(n)$) of an otoacoustic emission (OAE) for a continuous in-ear hearing health monitoring on a human being and using first and second in-ear earpieces being worn by a user, each said earpiece having an internal microphone (IEM-I, IEM-C) adapted to be in fluid communication with an outer ear canal of a respective ear of the user, an outer ear microphone (OEM-I, OEM-C) adapted to be in fluid communication with an adjacent environment outside the respective ear of the user, and first and second receivers adapted to be in fluid communication with the outer ear canal, first ($f_1(n)$) and ($f_2(n)$) second stimuli sound signals being simultaneously respectively sent to the first and second receivers of the first earpiece adapted for being worn in a tested ear of the user, first inner ($d_1(n)$) and outer ($x_2(n)$) sound signals being respectively simultaneously recorded from the internal (IEM-I) and outer ear (OEM-I) microphones of the first earpiece, and second inner sound signal ($x_1(n)$) being simultaneously recorded from the internal microphone (IEM-C) of the second earpiece, the method comprising the steps of:

a) acquiring a first input signal based on the first inner ($d_1(n)$) sound signal;

b) performing a noise rejection of the first input signal with either 1) a first output ($y_1(n)$) from an inner-ear normalized least-mean square (NLMS) adaptive filtering of the second inner sound signal ($x_1(n)$) to get an inner-ear noise reduced OAE signal ($e_1(n)$) being a second input signal based on the first inner ($d_1(n)$) sound signal, or 2) a second output ($y_2(n)$) from an outer-ear normalized least-mean square (NLMS) adaptive filtering of the outer sound signal ($x_2(n)$) to get an outer-ear noise reduced OAE signal ($e_2(n)$) being a second input signal based on the first inner ($d_1(n)$) sound signal;

c) performing a noise rejection of the second input signal with either 1) a second output ($y_2(n)$) from an outer-ear normalized least-mean square (NLMS) adaptive filtering of the outer sound signal ($x_2(n)$) to get a outer-ear noise reduced OAE signal ($e_2(n)$) being the OAE signal, or 2) a first output ($y_1(n)$) from an inner-ear normalized least-mean square (NLMS) adaptive filtering of the second inner sound signal ($x_1(n)$) to get an inner-ear noise reduced OAE signal ($e_1(n)$) being the OAE signal ($s(n)$), respectively; and d) providing the OAE signal ($s(n)$).

In one embodiment, the in-ear earpieces are custom-fitted earpieces.

In one embodiment, step c) further includes processing the OAE signal ($s(n)$) with a band-pass filter set at the frequency of the OAE signal ($s(n)$) to enhance the OAE signal ($s(n)$).

In one embodiment, the method further includes, between step a) and step b), a step of processing at least one of the outer sound signal ($x_2(n)$) of the outer ear microphone (OEM-I) of the first earpiece and the second inner sound signal ($x_1(n)$) of the internal microphone (IEM-C) of the second earpiece with a low-pass filter set at a predetermined frequency to condition the at least one signal.

Other objects and advantages of the present invention will become apparent from a careful reading of the detailed description provided herein, with appropriate reference to the accompanying drawings.

BRIEF DESCRIPTION OF THE DRAWINGS

Further aspects and advantages of the present invention will become better understood with reference to the description in association with the following Figures, in which similar references used in different Figures denote similar components, wherein.

DETAILED DESCRIPTION OF THE INVENTION

With reference to the annexed drawings the preferred embodiment of the present invention will be herein described for indicative purpose and by no means as of limitation.

Figure 1:
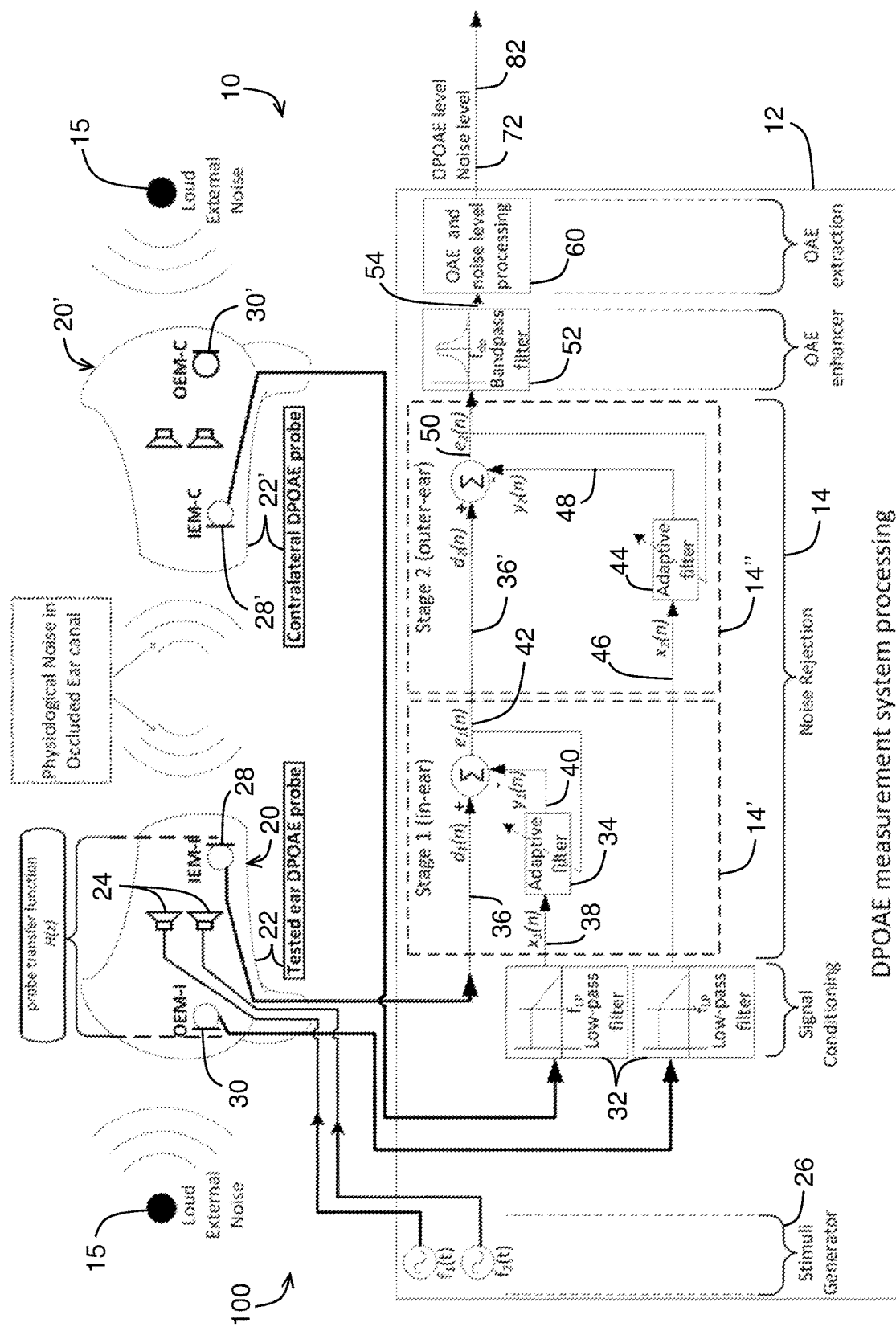
FIG. 1 is a schematic block diagram of a device and method for continuous in-ear hearing health monitoring on a human being in accordance with an embodiment of the present invention, further showing a noise rejection algorithm in accordance with an embodiment of the present invention and used in the device or method.

With reference to FIG. 1, there is shown a schematic block diagram of a device 10 and method 100 for continuous in-ear hearing health monitoring on a human being 11 (or user) in accordance with an embodiment of the present invention, and having a noise rejection, or adaptive filtering, algorithm 14 in accordance with an embodiment of the present invention and used in the device or method. The device 10 includes an earpiece 20 typically occluding the outer ear canal 13, 13', such as a custom-fitted earpiece body as an example, with an earpiece-embedded OAE probe 22, 22'. Each earpiece 20, 20', a pair of which is schematically shown in FIG. 1, includes two preferably high-quality miniature balanced armature receivers 24 (or also often called miniaturized loudspeakers) used to send the two pure-tone stimuli 26 ($f_1$ and $f_2$ with the $f_2/f_1$ ratio typically around 1.22) without any sound distortion from the DPOAE system controller 12. One miniature internal ear microphone 28, 28', IEM-I, IEM-C, is placed towards the ear canal 13, 13' in order to measure the otoacoustic emission response and physiological noise, respectively, and a miniature outer ear microphone 30, 30', OEM-I, OEM-C, is placed on the outside of the earpiece to measure the external background noise 15 (see FIG. 1). The two earpieces 20, 20' are typically connected to a signal conditioning circuit (not shown), part of the controller system 12, to amplify and filter the DPOAE microphone signal for the digital signal processor (not shown) (DSP—also part of the controller system 12) based data acquisition and digital signal processing circuit.

In the earpiece 20, 20', the tubing guiding the acoustical signal from the receivers/microphone to/from the probe's sound port ensures that acoustical crosstalk is eliminated as much as possible and background noise is reduced. Self-inflating custom molded earpieces fitted to ensure one's respective ear canals are preferably sealed or occluding the outer ear canal (maximum passive attenuation from the earpiece) for proper DPOAE measurements and also to protect the human subject when measuring in higher levels of background noise.

When tests with human subjects are being carried out on one ear of the subject, the corresponding earpiece 20 is used to measure the DPOAE (low-level cubic distortion signals (i.e. $f_{dp}=2f_1-f_2$) generated by an active non-linear process inside the inner ear) in that ear with the ipsilateral in-ear microphone 28 (IEM-I) and capture the external noise with the ipsilateral outer ear microphone 30 (OEM-I). Meanwhile, the other earpiece 20' is used to capture the physiological noise inside the other ear canal. It is assumed that the physiological noise is similar for both ear canals and since the other contralateral in-ear microphone 28' (IEM-C) does not capture the DPOAE responses evoked at the tested ear but only noise in the other ear canal, therefore in-ear microphone 28' (IEM-C) serves as a noise reference.

The adaptive filtering noise rejection (also signal denoising) algorithm 14 presented in FIG. 1 ensures that the noise measured in the DPOAE response when measuring DPOAEs in noisy conditions is reduced. A low-pass filter 32 is placed in the IEM-C and OEM-I signal paths in order to reduce the bandwidth of the noise signal to improve the adaptive filters convergence by focusing in lower frequencies where the earplug's passive attenuation is the least effective.

The Normalized version of the Least-Mean Square (NLMS) algorithm adaptive filter 34 in Stage 1 14' (inner-ear) models the transfer function between the tested ear in-ear microphone 28 (IEM-I) signal 36 ($d_1(n)$) and the contralateral in-ear microphone 28' (IEM-C) signal 38 ($x_1(n)$), or in-ear transfer function. The output signal 40 ($y_1(n)$) of this filter 34 is then subtracted from the desired signal input 36 ($d_1(n)$). The error signal 42 (On) is used to correct the adaptive filter's 34 coefficients in order to model the physiological noise disturbance in the tested ear's IEM-I accurately. In the $2^{nd}$ adaptive noise rejection stage 14" (Stage 2—outer-ear), the adaptive filter 44 models the DPOAE probe passive attenuation transfer function between tested ear in-ear microphone 28 (IEM-I) signal 36' ($d_2(n)$) and the tested ear outer ear microphone 30 (OEM-I) signal 46 ($x_2(n)$), or outer-ear transfer function. The input signal 46 ($x_2(n)$) of the adaptive filter 44 is the low-pass filtered OEM-I signal. The output signal 48 ($y_2(n)$) of the adaptive filter 44 is then subtracted from the tested ear's IEM-I signal 36' to remove the noise disturbance from the signal 36'. The output signal 48 ($y_2(n)$) of this filter 44 is then subtracted from the desired signal input 36' ($d_2(n)$). The error signal 50 ($e_2(n)$) is used to correct the adaptive filter's 44 coefficients.

A tracking band-pass filter 52 with frequency bandwidth centered on the DPOAE frequency is placed after the 2-stage adaptive filtering algorithm 14 to reject the primary tone stimuli signals 26 from the captured IEM-I signal 36. Stimuli rejection ensures proper functionality of the following DPOAE extraction algorithm 60 during otoacoustic emission measurements.

The above 2-stage adaptive filtering algorithm 14 is efficient to reject the noise in the OAE signals 36, 36' for industrial background noises up to about 110 dB(A), and typically at least about 80 dB(A). It is noted that the second stage 14" can also be performed before the first stage 14', without affecting the outcome of the adaptive filtering algorithm 14.

Figure 2:
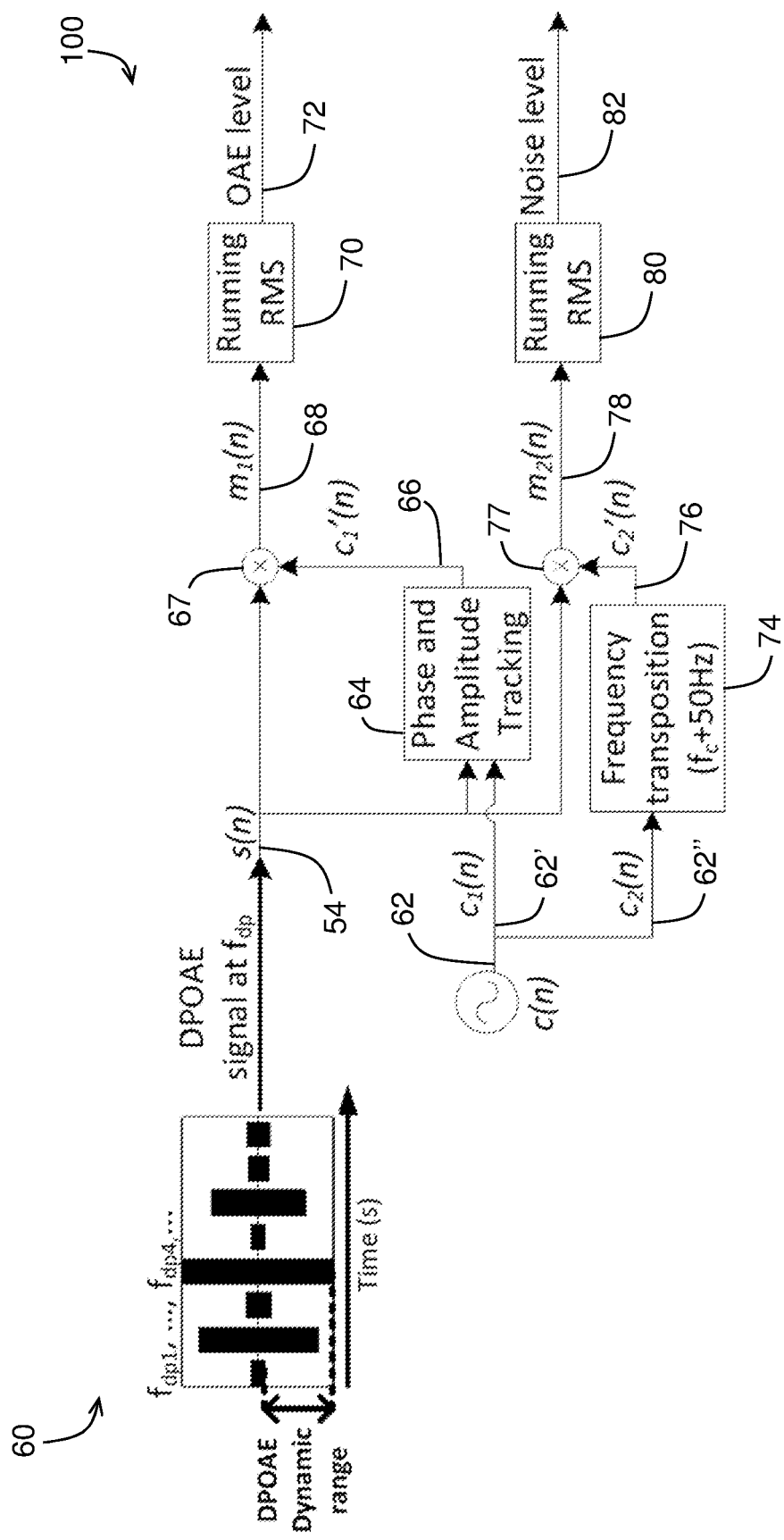
FIG. 2 is a schematic block diagram of a DPOAE signal extraction algorithm use in a device or method for continuous in-ear hearing health monitoring on a human being in accordance with an embodiment of the present invention.

Now referring more specifically to FIG. 2, there is shown a schematic diagram of a DPOAE signal extraction algorithm 60 used in a device 10 or method 100 for continuous in-ear hearing health monitoring on a human being in accordance with an embodiment of the present invention. In FIG. 2, the DPOAE response signal 54 (s(n)) represents the signal coming out of the adaptive filtering algorithm 14, 14', 14", shown in dashed lines, of FIG. 1.

The temporal modulation, more specifically an amplitude modulation (AM) algorithm estimates the DPOAE signal 54 without being affected by spectral leakage which occurs when the stimuli are not an integer multiple of the frequency resolution ($\Delta f$) of the FFT. This algorithm 60 has an automatic normalization (amplitude and phase tracking) process 64 that adjusts the modulating carrier signal 62 (c(n)) level to match the DPOAE signal (s(n)) level. An error signal (not shown) is calculated based on the difference between the captured DPOAE signal 54 (s(n)) and the generated modulation carrier signal 66 ($c_1'(n)$) after the normalization process 64, when this error signal exceeds a defined threshold, the phase of the modulation carrier is slightly adjusted to minimize this error. Another means of correcting the phase was also tested by the inventors, using cross-correlation to evaluate phase drifts. Any of the two methods can be used to correct for slight frequency variations, to sync the carrier signal 62' ($c_1(n)$) with the DPOAE signal 54 (s(n)) to extract. This way a maximum modulation index (h) is obtained, thus maximizing the DPOAE level dynamic range and minimizing the Root Mean Square Error (RMSE) of the estimated signal. The RMSE is the average of the estimation errors between the "true" level and the estimated level calculated across the typically twenty-two tested DPOAE frequencies used in order to benchmark the proposed algorithm with other estimator algorithms.

The present signal extraction algorithm 60, in being less sensitive to the frequency resolution of the system to extract the DPOAE signal 54 (s(n)) with the presence of stimuli signals 26, can be used to measure more DPOAE frequencies within a defined frequency range, therefore giving more information about the cochlea's health throughout the audible frequency range. This increase in DPOAE frequency resolution is especially useful for close monitoring of inner ear health changes in order to understand the recovery mechanisms of the human ear to a temporary hearing loss.

The present signal extraction algorithm 60 typically uses the band-pass Finite Impulse Response (FIR) filter 52 centered around the DPOAE frequency $f_{dp}$, shown in FIG. 1, to remove the stimuli signals 26 from the temporal signal prior to the modulation. The signal extraction algorithm 60 consists in the equations shown in the following section (Equations 1 to 7). The DPOAE signal 54 (s(n)) (see Equation 1) is modulated with a carrier signal 62 (c(n)) (see Equation 2) in order to estimate the magnitude of the DPOAE as a constant value (0 Hz).

$$s(n) = A_{dp} \sin(2\pi f_{dp} n t_s) \quad (1)$$

$$c(n) = A_c \sin(2\pi f_c n t_s + \quad (2)$$

To synchronize the carrier signal 62' ($c_1(n)$) with the DPOAE signal 54 (s(n)), the phase φ starts at π/2 and is increased by an additional delay within a loop until the error signal or cross-correlation (Equation 3a or 3b) gives the optimal result. When the error signal reaches a value below the defined threshold the phase adjustment is stopped. On the other hand, the cross-correlation can also be used as a measure of similarity between the DPOAE signal 54 and the carrier signal 62 as a function of the time difference between the signals on a frame of sample size (M).

$$e(n) = s(n) - c_1'(n) \quad (3a)$$

$$(c_1'^*s)(n) = \text{SUM}\_\{m=0\}^\wedge\{m=M/2-n\}(c_1'^*(m)s(m+n)) \quad (3b)$$

A running Root-Mean Square (RMS) value gives the magnitude of the signal over a certain amount of cycles of the sinusoid signal. The RMS value of the signal is calculated with a rectangular window w(n) with length W (Equation 4).

$$\text{rms}(s(n),w(n)) = \text{SQRT}[(s^2(n)w(n))/\text{SUM}\_\{n=0\}^\wedge\{W\}(w(n))] \quad (4)$$

$$c_1'(n) = [[\text{SUM}\_\{n=0\}^\wedge\{M\}\text{rms}(s(n),w(n))]/[\text{SUM}\_\{n=0\}^\wedge\{M\}\text{rms}(c_1(n),w(n))]]^*c_1(n) \quad (5)$$

The modulating carrier signal 66 ($c_1'(n)$) is then normalized based on the RMS value of the DPOAE signal 54 (see Equation 5). The normalization process 64 reduces the error between the DPOAE signal 54 and the carrier signal 62. It also results in a maximized cross-correlation if this is the algorithm used. This way, the modulation index (h), which corresponds to the ratio between the DPOAE signal magnitude and the carrier signal, is maximum (h=1) and the modulated DPOAE signal 68 ($m_1(n)$) has an optimal output, which means that the DPOAE signal estimation error is minimized.

$$m_1(n) = s(n) \cdot c_1'(n) \quad (6)$$

$$m_1(n) = (A_{dp}A_c/2)\sin(2\pi(f_{dp}-f_c)nt_s - \varphi \quad (7)$$

The constant (0 Hz) DPOAE signal 68 ($m_1(n)$) obtained (see Equations 6 and 7) is then filtered by the low-pass filter effect of a running RMS 70 algorithm to remove the undesired signals such as the $\sin(2\pi(f_{dp}+f_c')nt_s+\varphi)$ component of the modulated DPOAE signal 68 ($m_1(n)$), modulated via the modulator 67, and average the output for a constant magnitude DPOAE level estimation 72.

The AM algorithm 60 can also be used as an estimator to evaluate the noise around the DPOAE frequency. The noise estimator output 82 consists in the average of the modulated noise signal 78 ($m_2(n)$). The modulated noise signal 78 ($m_2(n)$) is the result of the modulation of the DPOAE signal 54 (s(n)) with the transposed modulating carrier signal 76 ($c_2'(n)$), $m_2(n) = s(n) \cdot c_2'(n)$. The frequency transposition 74 for ($c_2(n)$) is used to modulate, via the modulator 77, the noise contained in the upper frequency band adjacent to the DPOAE signal 54 to frequencies equal or higher than 0 Hz. The frequency transposition 74 typically transposes the frequency of the carrier signal 62" (c2(n)) into the transposed modulating carrier signal 76 ($c_2'(n)$) by a frequency step varying from about 5 Hz to about 100 Hz, and preferably of about 50 Hz. After modulation 77, the constant (0 Hz) noise signal 78 ($m_2(n)$) magnitude is averaged using running RMS 80 which estimates the noise level 82 afterwards.

According to previous simulations, the envisioned DPOAE signal extraction algorithm 60 is reliable and robust (lower estimation error), mostly for lower noise floors (−12 to −8 dB(SPL)) down to a RMSE of about 2.0 dB. The DPOAE signal extraction algorithm 60 also has a low and stable RMSE when the dynamic range of the DPOAE signal 54 to extract is increased. The RMSE of the present method is quite consistent over the tested ranges ([−5;5] to [−30;30] dB(SPL)) and lower than any known FFT RMSE for most of the dynamic ranges tested.

According to other previous simulations, the signal extraction method 60 is more immune to spectral leakage (RMSE around 3 dB for the present algorithm vs RMSE around 5 dB for the FFT). Therefore, it can be used as an estimator when stimuli frequencies and DPOAE frequencies are not an integer multiple of the systems frequency resolution (Δf) and cause spectral leakage. Thus, the present algorithm 60 can be used to detect changes in the cochlea's functionality with a greater frequency resolution (extended range of DPOAE's) than FFT based methods commonly used in commercial systems since the stimuli frequencies can be set without restrictions.

The present signal extraction algorithm 60 is also slightly more robust than known algorithms in lower noise conditions. Overall, the present algorithm has the most stable RMSE in different DPOAE dynamic range. In addition, the present algorithm needs no parameter adjustment and still gives a lower RMSE than known algorithms, therefore it can be fully autonomous, robust and accurate in a field application.

Finally, a faster convergence time (about 0.2 s) of the present signal extraction algorithm reduces the total measurement time required to about a half, for the whole DPOAE frequency range, when compared to known algorithms which typically have a convergence time larger than about 0.5 s.

The present algorithm 60 using temporal modulation for the extraction of DPOAE levels is designed for small and low cost DSPs and can be used to measure an extended range of DPOAE frequencies. This way a portable DPOAE measurement system can be used to characterize the functionality of the inner ear more precisely. The lower RMSE of the present algorithm is especially helpful to detect slight changes in the cochlea's health accurately. Therefore, a portable continuous DPOAE monitoring device 10 including the present algorithm 60 can be used in field to detect slight changes in the cochlea's health in order to warn the wearer of a potential change in hearing functionality, hence preventing a permanent hearing threshold shift. Accordingly, the output media onto which the different output results are provided and/or displayed can be any known media, and preferably portable media, such as, but not limited to, laptop computers, tablets, smartphones, personal digital assistants (PDAs), or the like.

Figure 3:
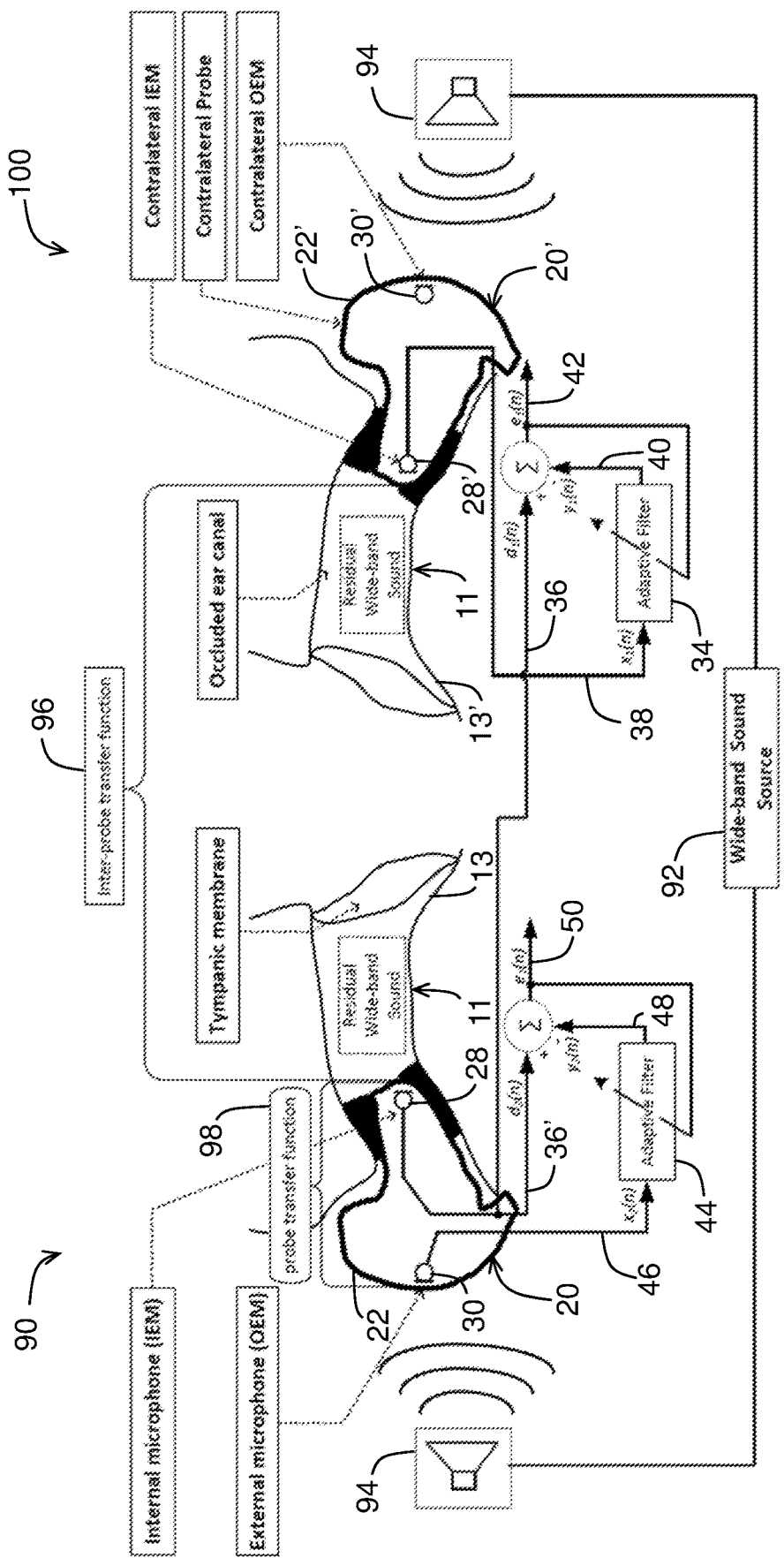
FIG. 3 is a schematic block diagram of an initialization step of the adaptive filters used in the noise rejection algorithm of the device or method for continuous in-ear hearing health monitoring on a human being in accordance with the embodiment of FIG. 1.

Now referring more specifically to FIG. 3, there is shown an adaptive filter coefficient initialization method 90 in accordance with an embodiment of the present invention. Where an external wide-band sound signal 92 covering the audible frequency range (typically between about 20 Hz and about 20 kHz) is sent to an external loudspeaker 94 for a pre-determined time duration, varying between about 1 s and about 300 s (preferably less than 120 s), while activating the adaptation of the inter-probe transfer function adaptive filter 34 using the respective inner sound signals 36, 38 ($d_1(n)$, $x_2(n)$) measured from the internal (IEM-I, IEM-C) microphones 28, 28' of the first 20 and second 20' earpieces worn by the user 11 and the probe attenuation transfer function adaptive filter 44 using the respective inner 36' ($d_2(n)$) and outer 46 ($x_2(n)$) sound signals measured from the internal 28 (IEM-I) and outer ear 30 (OEM-I) microphones of the first earpiece. Activation of the adaptation allows the coefficients of the respective adaptive filters 34, 44 to converge using a small step size in order to minimize the respective error signals 42, 50 ($e_1(n)$, $e_2(n)$), therefore identifying respective acoustical paths between internal (IEM-I, IEM-C) microphones, here called inter-probe transfer function 96, and between the internal (IEM-I) and outer ear (OEM-I) microphones, here called probe attenuation transfer function 98 or simply probe transfer function. The adaptation includes using a convergence step size varying typically between about 0.0001 and about 0.7

During such adaptive filter coefficient initialization step, the first ($f_1(n)$) and second ($f_2(n)$) stimuli sound signals must be completely stopped in order to prevent the convergence of the adaptive filters on such primary tones. After the pre-determined time duration allowed for convergence is finished, the external wide-band sound signal 92 and the adaptation of the inter-probe 96 and probe attenuation 98 transfer functions are stopped.

The initialized inter-probe transfer function 96 of the first adaptive filter 34 and the initialized probe attenuation transfer function 98 of the second adaptive filter 44 are used by the noise rejection algorithm 14 in the real-time processing of DPOAE signals 54 when first ($f_1(n)$) and second ($f_2(n)$) stimuli sound signals are present, but adaptation the transfer functions 96, 98 is stopped. Adaptation of the inter-probe transfer function 96 and probe attenuation transfer function 98 can be re-activated, after first initialization and while first ($f_1(n)$) and second ($f_2(n)$) stimuli sound signals are stopped, without necessitating an external wide-band sound 92, in order to adjust for slight variations in the acoustical paths that might occur due to body movements for example while the earpieces 20, 20' are worn and therefore minimizing the error in the DPOAE signal 54 that could come from such slight variations in the transfer functions 96, 98.

Although the present invention has been described with a certain degree of particularity, it is to be understood that the disclosure has been made by way of example only and that the present invention is not limited to the features of the embodiments described and illustrated herein, but includes all variations and modifications within the scope of the invention as herein above described and hereinafter claimed.

We claim:

1. A device for continuous in-ear hearing health monitoring on a human being, the device comprising:
 a pair of earpieces, each said earpiece including an internal microphone (IEM-I, IEM-C) adapted to be in fluid communication with an outer ear canal of an ear of a user, an outer ear microphone (OEM-I, OEM-C) adapted to be in fluid communication with an adjacent environment outside the ear of the user, and first and second receivers adapted to be in fluid communication with the outer ear canal;
 a controller system connecting to both the first and second receivers of at least one said pair of earpieces for simultaneously sending first ($f_1(n)$) and second ($f_2(n)$) stimuli sound signals thereto, respectively, the controller system connecting to the internal and outer ear (IEM-I, OEM-I) of one said earpieces corresponding the a tested ear of the user and to the internal (IEM-C) microphone of the other one said earpieces for recording respective inner ($d_1(n)$), outer ($x_2(n)$) and inner ($x_1(n)$) sound signals therefrom; and
 an output media connected to the controller system for providing a resulting magnitude of a distortion product otoacoustic emission (DPOAE) signal calculated by the controller system using a noise rejection algorithm and a signal extraction algorithm based on a carrier signal ($c(n)$) at a frequency of the DPOAE signal established using the first ($f_1(n)$) and second ($f_2(n)$) stimuli sound signals.

2. The device of claim 1, wherein the outer ear microphone (OEM-I, OEM-C) are adapted to be located within a 15 cm distance from the outer ear of the user.

3. The device of claim 1, wherein the controller system includes a band-pass filter set at the frequency of the DPOAE signal to enhance the DPOAE signal as an input to the signal extraction algorithm.

4. The device of claim 1, wherein the controller system includes a low-pass filter set at a predetermined frequency to condition at least one of the outer ($x_2(n)$) sound signal of the outer ear microphone (OEM-I) and the inner ($x_1(n)$) sound signal of the internal microphone (IEM-C) before calculation of the DPOAE signal with the controller system using the noise rejection algorithm.

5. The device of claim 1, wherein the output media is a portable output media.

6. The device of claim 1, wherein the controller system is a portable controller system and the output media is a display of the portable controller system.

7. A method for continuous in-ear hearing health monitoring on a human being based on measurements of distortion product otoacoustic emission (DPOAE) signals and using a pair of first and second earpieces, each said earpiece having an internal microphone (IEM-I, IEM-C) adapted to be in fluid communication with an outer ear canal of an ear of a user, an outer ear microphone (OEM-I, OEM-C) adapted to be in fluid communication with an adjacent environment outside the ear of the user, and first and second receivers adapted to be in fluid communication with the outer ear canal, the method comprising the steps of:
 a) sending simultaneously first ($f_1(n)$) and second ($f_2(n)$) stimuli sound signals to the first and second receivers of the first earpiece of a tested ear of the user, respectively;
 b) simultaneously recording respective inner ($d_1(n)$) and outer ($x_2(n)$) sound signals from the internal and outer ear microphones (IEM-I, OEM-I) of the first earpiece and an inner sound signal ($x_1(n)$) from the internal microphone (IEM-C) of the second earpiece; and
 c) processing the inner ($d_1(n)$, $x_1(n)$) and outer ($x_2(n)$) sound signals of said first and second earpieces to obtain a resulting distortion product otoacoustic emission (DPOAE) signal based on the first ($f_1(n)$) and second ($f_2(n)$) stimuli sound signals and using a noise rejection algorithm followed by a signal extraction algorithm.

8. The method of claim 7, further including, before step a), the steps of:
- initializing an inter-probe transfer function of a first adaptive filter using the internal (IEM-I, IEM-C) microphones of the first and second earpieces and a probe attenuation transfer function of a second adaptive filter using the internal (IEM-I) and outer ear (OEM-I) microphones of the first earpiece when only an external wide-band sound signal is being sent to an external loudspeaker for a pre-determined time duration;
- sending only an external wide-band sound signal to an external loudspeaker;
- activating an adaptation of the inter-probe transfer function using the respective inner sound signals ($d_1(n)$, $x_2(n)$) measured from the internal (IEM-I, IEM-C) microphones of the first and second earpieces and the probe attenuation transfer function using the respective inner ($d_1(n)$) and outer ($x_2(n)$) sound signals measured from the internal (IEM-I) and outer ear (OEM-I) microphones of the first earpiece with the external wide-band sound signal for a pre-determined time duration; and
- stopping sending the external wide-band sound signal and the adaptation of the inter-probe and probe attenuation transfer functions;
- wherein the initialized inter-probe transfer function of the first adaptive filter and the initialized probe attenuation transfer function of the second adaptive filter are used by the noise rejection algorithm in the processing step c).

9. The method of claim 8, wherein the step of activating an adaptation includes using a convergence step size varying between about 0.0001 and about 0.7.

10. The method of claim 8, wherein the external wide-band sound signal covers a frequency range extending between about 20 Hz and about 20 kHz.

11. The method of claim 7, wherein step c) further includes processing a noise rejection filtered DPOAE signal with a band-pass filter set at the frequency of the DPOAE signal to enhance the DPOAE signal as an input to the signal extraction algorithm.

12. The method of claim 7, wherein step c) further includes processing at least one of the outer ($x_2(n)$) sound signal of the outer ear microphone (OEM-I) and the inner ($x_1(n)$) sound signal of the internal microphone (IEM-C) with a low-pass filter set at a predetermined frequency to condition before processing the inner ($d_1(n)$, $x_1(n)$) and outer ($x_2(n)$) sound signals of said first and second earpieces using the noise rejection algorithm.

13. The method of claim 7, further including the step of:
- d) providing the resulting DPOAE signal onto an output media.

14. The method of claim 13, wherein the step of providing includes providing the resulting DPOAE signal onto a portable output media.

15. The method of claim 8, wherein the pre-determined time duration varies between about 1 s and about 300 s.

16. The method of claim 15, wherein the pre-determined time duration is about 120 s.

17. A signal noise rejection method for providing a signal ($s(n)$) of an otoacoustic emission (OAE) for a continuous in-ear hearing health monitoring on a human being and using first and second in-ear earpieces being worn by a user, each said earpiece having an internal microphone (IEM-I, IEM-C) adapted to be in fluid communication with an outer ear canal of a respective ear of the user, an outer ear microphone (OEM-I, OEM-C) adapted to be in fluid communication with an adjacent environment outside the respective ear of the user, and first and second receivers adapted to be in fluid communication with the outer ear canal, first ($f_1(n)$) and ($f_2(n)$) second stimuli sound signals being simultaneously respectively sent to the first and second receivers of the first earpiece adapted for being worn in a tested ear of the user, first inner ($d_1(n)$) and outer ($x_2(n)$) sound signals being respectively simultaneously recorded from the internal (IEM-I) and outer ear (OEM-I) microphones of the first earpiece, and second inner sound signal ($x_1(n)$) being simultaneously recorded from the internal microphone (IEM-C) of the second earpiece, the method comprising the steps of:
- a) acquiring a first input signal based on the first inner ($d_1(n)$) sound signal;
- b) performing a noise rejection of the first input signal with either 1) a first output ($y_1(n)$) from an inner-ear normalized least-mean square (NLMS) adaptive filtering of the second inner sound signal ($x_1(n)$) to get an inner-ear noise reduced OAE signal ($e_1(n)$) being a second input signal based on the first inner ($d_1(n)$) sound signal, or 2) a second output ($y_2(n)$) from an outer-ear normalized least-mean square (NLMS) adaptive filtering of the outer sound signal ($x_2(n)$) to get an outer-ear noise reduced OAE signal ($e_2(n)$) being a second input signal based on the first inner ($d_1(n)$) sound signal;
- c) performing a noise rejection of the second input signal with either 1) a second output ($y_2(n)$) from an outer-ear normalized least-mean square (NLMS) adaptive filtering of the outer sound signal ($x_2(n)$) to get a outer-ear noise reduced OAE signal ($e_2(n)$) being the OAE signal, or 2) a first output ($y_1(n)$) from an inner-ear normalized least-mean square (NLMS) adaptive filtering of the second inner sound signal ($x_1(n)$) to get an inner-ear noise reduced OAE signal ($e_1(n)$) being the OAE signal ($s(n)$), respectively; and
- d) providing the OAE signal ($s(n)$).

18. The method of claim 17, wherein the in-ear earpieces are custom-fitted earpieces.

19. The method of claim 17, wherein step c) further includes processing the OAE signal ($s(n)$) with a band-pass filter set at the frequency of the OAE signal ($s(n)$) to enhance the OAE signal ($s(n)$).

20. The method of claim 17, further including, between step a) and step b), a step of processing at least one of the outer sound signal ($x_2(n)$) of the outer ear microphone (OEM-I) of the first earpiece and the second inner sound signal ($x_1(n)$) of the internal microphone (IEM-C) of the second earpiece with a low-pass filter set at a predetermined frequency to condition the at least one signal.

* * * * *